United States Patent
Buchta et al.

(10) Patent No.: US 12,263,235 B2
(45) Date of Patent: Apr. 1, 2025

(54) COMPOSITIONS FOR REMOVING ARTIFICIAL TAN

(71) Applicant: BONDI SANDS PTY LTD, Victoria (AU)

(72) Inventors: Richard Buchta, Victoria (AU); Rose Ye, Victoria (AU); Claire Dinh, Victoria (AU); Robert Houlden, Victoria (AU)

(73) Assignee: BONDI SANDS PTY LTD, Victoria (AU)

( * ) Notice: Subject to any disclaimer, the term of this patent is extended or adjusted under 35 U.S.C. 154(b) by 0 days.

(21) Appl. No.: 16/615,410

(22) PCT Filed: May 25, 2018

(86) PCT No.: PCT/AU2018/050510
§ 371 (c)(1),
(2) Date: Nov. 21, 2019

(87) PCT Pub. No.: WO2018/213892
PCT Pub. Date: Nov. 29, 2018

(65) Prior Publication Data
US 2020/0163853 A1 May 28, 2020

(30) Foreign Application Priority Data

May 26, 2017 (AU) ................................. 2017902007
Jul. 24, 2017 (AU) ................................. 2017902887

(51) Int. Cl.
*A61K 8/42* (2006.01)
*A61K 8/02* (2006.01)
(Continued)

(52) U.S. Cl.
CPC .............. *A61K 8/42* (2013.01); *A61K 8/0208* (2013.01); *A61K 8/042* (2013.01); *A61K 8/046* (2013.01); *A61K 8/06* (2013.01); *A61Q 19/00* (2013.01)

(58) Field of Classification Search
None
See application file for complete search history.

(56) References Cited

U.S. PATENT DOCUMENTS 5,720,961 A * 2/1998 Fowler .................... A61K 8/88
514/846
6,827,943 B2 12/2004 Glassman et al.
(Continued)

FOREIGN PATENT DOCUMENTS

CN 1257713 A * 6/2000
CN 106176420 A 12/2016
(Continued)

OTHER PUBLICATIONS

Banerjee "Topical urea in dermatology", Indian J. Dermato. Mar. 35(1): 17-24 (Year: 1990).*
(Continued)

*Primary Examiner* — Isis A Ghali
(74) *Attorney, Agent, or Firm* — Frost Brown Todd LLP

(57) ABSTRACT

Artificial tan removal compositions, methods of preparation and methods of use are provided. The tan removal compositions contain urea and are alkaline in pH. The compositions are effective at removing artificial tan from skin rapidly and in a single application. The compositions are substantially stable over long periods of time.

20 Claims, 1 Drawing Sheet

(51) Int. Cl.
*A61K 8/04* (2006.01)
*A61K 8/06* (2006.01)
*A61Q 19/00* (2006.01)

(56) References Cited

U.S. PATENT DOCUMENTS

| | | |
|---|---|---|
| 2003/0064084 A1 | 4/2003 | Bhagwat et al. |
| 2003/0099678 A1 | 5/2003 | Maibach et al. |
| 2003/0235542 A1* | 12/2003 | Maibach ............ A61K 8/19 424/62 |
| 2013/0224137 A1* | 8/2013 | Kvalnes ............ A61Q 5/08 424/62 |
| 2015/0004108 A1* | 1/2015 | Campache ......... A61K 8/9789 424/59 |

FOREIGN PATENT DOCUMENTS

| | | |
|---|---|---|
| EP | 0101887 A2 | 3/1984 |
| JP | H0797326 A | 4/1995 |

OTHER PUBLICATIONS

Banerjee "Topical Urea in Dermatology", Indian J. Dermato. Mar. 35(1):17-24, full document. (Year: 1990).*

International Search Report and Written Opinion issued in corresponding International Patent Application No. PCT/AU2018/050510 mailed Jul. 24, 2018 (8 pages).

Self Tan Removal Cream, Record ID 543655, Novalle, Orange Palms Preventor, Mintel, 2006, http://www.gnpd.com.

Tan Remover, Record ID 2158245, Superdrug, Superdrug Solait, Mintel, 2013, http://www.gnpd.com.

* cited by examiner

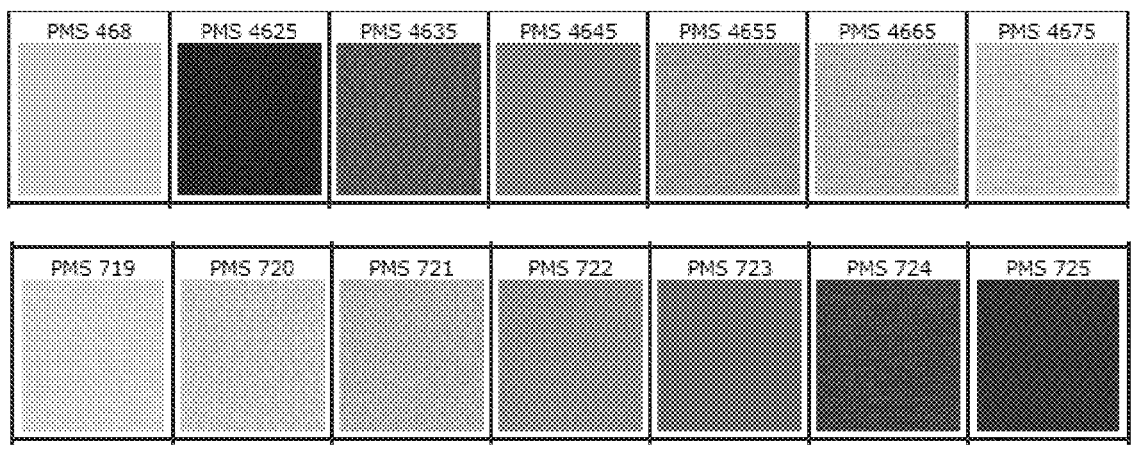

COMPOSITIONS FOR REMOVING ARTIFICIAL TAN

FIELD

The present disclosure relates to cosmetic or pharmaceutical compositions and methods for their preparation. In particular the present disclosure relates to compositions for removing an artificial tan wherein the compositions comprise urea.

BACKGROUND

A sun-tanned appearance has been a symbol of a healthy, dynamic, and active life for many years. Yet, the damaging effects of sunlight and artificial sources of ultraviolet radiation on the skin are well documented. Furthermore these effects are cumulative and potentially serious. These effects include sunburn, skin cancer and premature aging of the skin.

Furthermore, even if an individual is willing to accept the risks associated with exposure to ultraviolet radiation to obtain a tan, there are situations in which it may not be practical or even possible to do so because of time constraints, weather conditions, time of day, season of the year, geographic location, unavailability of an artificial ultraviolet radiation source, and the like. Therefore, products have been developed that can deliver a tanned appearance whenever desired without the need for ultraviolet radiation.

It is generally known that certain compounds when applied topically to human skin will produce a tanned appearance, that is, an artificial tan. U.S. Pat. No. 4,708,865 describes the use of solutions of dihydroxyacetone for tanning the skin. U.S. Pat. No. 4,466,805 describes hair and skin coloring formulations containing dihydroxyacetone, and U.S. Pat. No. 2,949,403 describes artificial tanning formulations containing dihydroxyacetone. Dihydroxyacetone is believed to provide an artificial tan to human skin by its reaction with the nitrogen containing proteins of the skin. Other compositions which produce an artificial tan include erythrulose and caramel based dyes.

However, some artificial tanning products have the disadvantage of not providing the desired control over colour development of the tan. Artificial tans are sometimes too light or too dark, uneven, or unnatural in appearance. Furthermore, artificial tans can take a long period to develop, and once obtained, can fade too quickly and unevenly. In view of these issues the user may have a change of mind after applying the product.

Accordingly, the situation often arises in which people wish to deliberately remove an artificial tan. Numerous methods are available in the art, ranging from vigorous physical scrubbing to various home remedies, such as lemon juice. US 20060161121 discloses a bleaching composition comprising peroxide for bleaching chemically tanned skin. These methods, however, are generally inefficient in removing the tan. Further, acidic tan removal compositions are irritating to skin. Products have been marketed, but they typically require multiple application steps, thus adding to the time of removal. Stability of tan removal compositions is also an important retail consideration, particularly in regard to extended product shelf-life.

It would therefore be desirable to provide alternative cosmetic compositions and methods effective for artificial tan removal, particularly compositions and methods for removing an artificial tan which address one or more of the above highlighted problems and deficiencies.

The reference in this specification to any prior publication (or information derived from it), or to any matter which is known, is not, and should not be taken as an acknowledgement or admission or any form of suggestion that that prior publication (or information derived from it) or known matter forms part of the common general knowledge in the field of endeavour to which this specification relates.

SUMMARY

Artificial Tan Remover

In a first aspect, there is provided an artificial tan remover comprising:
  up to about 30% by weight of urea, a substituted derivative of urea, or mixtures thereof, based on the total weight of the tan remover; and
  the balance as water;
  wherein the tan remover has a pH greater than 7.0.

In a second aspect, there is provided an artificial tan remover comprising:
  one or more bases; and
  the balance as water;
  wherein the tan remover has a pH greater than 7.0.

In a third aspect, there is provided an artificial tan remover comprising:
  up to about 30% by weight of urea, a substituted derivative of urea, or mixtures thereof, based on the total weight of the tan remover;
  one or more bases; and
  the balance as water;
  wherein the tan remover has a pH greater than 7.0.

In a fourth aspect, there is provided an artificial tan remover comprising:
  up to about 30% by weight of urea, a substituted derivative of urea, or mixtures thereof, based on the total weight of the tan remover; and
  the balance as water;
  wherein the tan remover has a pH greater than 7.0; and
  wherein the amount of urea in the tan remover decreases by less than 20% by weight, or less than 15% by weight, or less than 10% by weight, or less than 5% by weight, when the tan remover is stored at 40° C. for one month.

In any of the herein disclosed aspects the amount of urea in the tan remover may decrease by less than 20% by weight, or less than 15% by weight, or less than 10% by weight, or less than 8% by weight, when the tan remover is stored at 40° C. for two months.

In any of the herein disclosed aspects the amount of urea in the tan remover may decrease by less than 20% by weight, or less than 15% by weight, or less than 10% by weight, when the tan remover is stored at 40° C. for three months.

In any of the herein disclosed aspects the amount of urea in the tan remover may decrease by less than 20% by weight, or less than 15% by weight, when the tan remover is stored at 40° C. for six months or for twelve months.

In any of the herein disclosed aspects the amount of urea in the tan remover may be substantially unchanged when the tan remover is stored at 5° C. for six months. For example, the amount of urea may decrease by less than 5% by weight, or less than 4% by weight, or less than 3% by weight when the tan remover is stored at 5° C. for six months.

In any of the herein disclosed aspects the amount of urea in the tan remover may be substantially unchanged when the tan remover is stored at ambient temperature, for example, 23° C., for twelve months. For example, the amount of urea may decrease by less than 5% by weight, or less than 4% by weight, or less than 3% by weight when the tan remover is stored at ambient temperature, for example, 23° C., for twelve months.

In a fifth aspect, there is provided an artificial tan remover comprising:
up to about 30% by weight of urea, a substituted derivative of urea, or mixtures thereof, based on the total weight of the tan remover;
one or more bases; and
the balance as water;
wherein the tan remover has a pH greater than 7.0; and
wherein the amount of urea in the tan remover decreases by less than 20% by weight, or less than 15% by weight, or less than 10% by weight, or less than 5% by weight, when the tan remover is stored at 40° C. for one month.

The amount of urea in the tan remover may decrease by less than
20% by weight, or less than 15% by weight, or less than 10% by weight, or less than 8% by weight, when the tan remover is stored at 40° C. for two months.

The amount of urea in the tan remover may decrease by less than 20% by weight,
or less than 15% by weight, or less than 10% by weight, when the tan remover is stored at 40° C. for three months.

The amount of urea in the tan remover may decrease by less than 20% by weight,
or less than 15% by weight, when the tan remover is stored at 40° C. for six months or for 12 months.

The amount of urea in the tan remover may be substantially unchanged when the tan remover is stored at ambient temperature, for example, 23° C., for twelve months. For example, the amount of urea may decrease by less than 5% by weight, or less than 4% by weight, or less than 3% by weight when the tan remover is stored at ambient temperature, for example, 23° C. for twelve months.

The amount of urea in the tan remover may be substantially unchanged when the tan remover is stored at 5° C. for six months. For example, the amount of urea may decrease by less than 5% by weight, or less than 4% by weight, or less than 3% by weight when the tan remover is stored at 5° C. for six months.

In any one of the herein disclosed aspects or embodiments the pH of the tan remover may change by less than 1 pH unit, or less than 0.5 pH units, or less than 0.3 pH units, or less than 0.2 pH units when the tan remover is stored for 12 months at ambient temperature, for example, 23° C.

Advantages of the Present Artificial Tan Remover

The artificial tan remover of the present disclosure may possess one or more of the following advantages compared to prior art artificial tan removers.
it is effective in removing artificial tan with a single application.
artificial tan removal is effected in only one step with a single product.
removal of the artificial tan is fast, typically in less than five minutes.
artificial tan removal does not require abrasion or exfoliation.
the artificial tan remover is non-irritating to the skin.
the artificial tan remover has excellent long term stability
the artificial tan remover is cosmetically and aesthetically appealing.

The artificial tan remover as herein disclosed is particularly effective at removing artificial tan derived from typically available artificial tanning products, for example artificial tanning products comprising dihydroxyacetone.

The artificial tan remover according to any one of the herein disclosed embodiments substantially retains its ability to remove an artificial tan after storing at 40° C. for six months. This equates to storage for about two years at ambient temperature. This is extremely advantageous in respect of extended product shelf life.

By 'substantially retains' it may be meant that there is no perceptible visual distinction between the artificial tan removing ability of a freshly prepared artificial tan remover according to the present disclosure compared to the tan remover which has been stored for six months at 40° C. or at ambient temperature, for example, 23° C., for twelve months.

In any one of the first to fifth aspects, the urea, or substituted derivative of urea, may be represented by the formula:

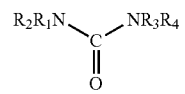

wherein $R_1$, $R_2$, $R_3$ and $R_4$ are independently selected from hydrogen, a $C_1$-$C_4$ alkyl group, a $C_1$-$C_4$ alkyl group substituted with one or more of amine, ester, carboxyl, alkoxy or halide, and a $C_2$-$C_6$ hydroxyalkyl group containing from 1 to 5 hydroxyl groups.

In any one of the first to fifth aspects the artificial tan remover may have a pH greater than or equal to about 7.5, or greater than or equal to about 8.0, or greater than or equal to about 8.5, or greater than or equal to about 9, or greater than or equal to about 9.5, or greater than or equal to 11.0.

In any one of the first to fifth aspects the artificial tan remover may have a pH in the range from about 7.0 to about 12.0, or from about 7.0 to about 11.0, or from about 7.0 to about 10.0, or from about 8.0 to about 12.0, or from about 8.0 to about 11.0, or from about 8.0 to about 10.0, or from about 8.5 to about 9.5, or from about 9.0 to about 9.5.

In any one of the first to fifth aspects the artificial tan remover may comprise about 0.1% to about 30% by weight of urea, a substituted derivative of urea, or mixtures thereof, based on the total weight of the artificial tan remover. The artificial tan remover may comprise about 5% to about 15% by weight of urea, a substituted derivative of urea, or mixtures thereof, based on the total weight of the artificial tan remover. The artificial tan remover may comprise about 7% to about 13% by weight of urea, a substituted derivative of urea, or mixtures thereof, based on the total weight of the artificial tan remover. In other embodiments the artificial tan remover may comprise about 1% to about 10% by weight of urea, a substituted derivative of urea, or mixtures thereof, or about 2% to about 7%, based on the total weight of the artificial tan remover.

As used herein the term "base" may refer to a compound that can accept a proton when dissolved in a protic solvent. When present, the artificial tan remover may comprise one or more weak bases.

When present, the one or more bases may be any pH adjuster that shifts pH above 7.0, that is, an alkaline pH adjuster. When present, the one or more bases may be selected from metal salts, such as hydroxides, carbonates, bicarbonates or selected from phosphates, ammonia, amino acids or amines.

When present, the one or more bases may be selected from one or more
alkali metal and alkaline earth salts. The alkali metal and alkaline earth salts may be selected from one or more carbonate and bicarbonate salts. Preferred bases include alkali metal hydroxides, carbonates and bicarbonates. Exemplary bases include sodium hydroxide, sodium carbonate and sodium bicarbonate. Other exemplary bases include potassium hydroxide, triethanolamine, 2-amino-2-hydroxymethyl-1,3-propanediol, disodium phosphate, ammonium hydroxide, trisodium citrate or tetrasodium EDTA, or amino acids, such as, for example, arginine, lysine or histidine.

When present, the artificial tan remover may comprise up to about 30% by weight of one or more bases, or up to about 20% by weight, or up to about 15% by weight or up to about 10% by weight, based on the total weight of the artificial tan remover. The artificial tan remover may comprise about 1 to about 10% by weight of one or more bases, or about 2 to 7% by weight of one or more bases, or about 1% to about 5%.

In any one of the first to fifth aspects the artificial tan remover may further comprise one or more skin penetration enhancers. The skin penetration enhancer may be selected from one or more alcohols, glycols, polyols, fatty acids, surfactants, ether alcohols, cyclic ether alcohols, alkoxy substituted cyclic ethers and fatty alcohol esters.

The artificial tan remover may comprise up to 30% by weight of one or more skin penetration enhancers, based on the total weight of the artificial tan remover. The skin penetration enhancer may be present in an amount of about 1 to about 20% by weight, or about 3 to about 10%, based on the total weight of the artificial tan remover.

In any one of the first to fifth aspects the artificial tan remover may further comprise one or more surfactants. The surfactant may be an anionic surfactant, a cationic surfactant, a non-ionic surfactant, an amphoteric surfactant, or mixtures thereof.

The artificial tan remover may comprise up to 50% by weight of one or more surfactants based on the total weight of the artificial tan remover, or up to 20% by weight, or up to 10% by weight. The artificial tan remover may comprise about 2% to about 20% by weight surfactant, or about 5 to about 20% by weight surfactant, or about 5 to about 20% by weight, or about 5 to about 15% by weight, based on the total weight of the artificial tan remover.

In any one of the first to fifth aspects the artificial tan remover may comprise one or more acceptable carriers and excipients, including preservatives, anti-oxidants, anti-inflammatories, emollients, moisturisers, sun screen agents, buffers, humectants, solubilisers, fragrances, exfoliants, colourants, metal ions, viscosity modifying agents and essential oils, selected to facilitate and/or enhance application, removal, user experience and/or efficacy. Other agents may be contemplated. The further components are preferably miscible and compatible and do not detract from the function of urea as herein described or detract from the stability and function of the artificial tan remover.

The metal ions may comprise one or more transition metal or non-transition metal ions. The metal ions may be capable of complexing with melanoidins. The metal ions may aid in the removal of melanoidins, for example, by precipitating them as complex salts. The metal ions may be in the form of one or more metal complexes.

Up to about 10% by weight of metal ions may be present in the tan remover, preferably up to about 5% by weight, based on the total weight of the tan remover.

In an embodiment, the artificial tan remover comprises:
up to about 30% by weight of urea;
up to about 20% by weight of a bicarbonate or carbonate salt; and
the balance as water;
wherein the tan remover has a pH greater than 7.0.

In an embodiment, the artificial tan remover comprises:
up to about 30% by weight of urea;
up to about 20% by weight of a bicarbonate or carbonate salt; and
the balance as water;
wherein the tan remover has a pH greater than 8.0.

In an embodiment, the artificial tan remover comprises:
up to about 30% by weight of urea;
up to about 20% by weight of a bicarbonate or carbonate salt; and
the balance as water;
wherein the tan remover has a pH greater than 9.0.

In an embodiment, the artificial tan remover comprises:
up to about 30% by weight of urea;
up to about 20% by weight of a bicarbonate or carbonate salt; and
the balance as water;
wherein the tan remover has a pH greater than 7.0; and
wherein the amount of urea in the tan remover decreases by less than 20% by weight, or less than 15% by weight, or less than 10% by weight, or less than 5% by weight, when the tan remover is stored at 40° C. for one month.

The amount of urea in the tan remover may decrease by less than 20% by weight,
or less than 15% by weight, or less than 10% by weight, or less than 8% by weight, when the tan remover is stored at 40° C. for two months.

The amount of urea in the tan remover may decrease by less than 20% by weight,
or less than 15% by weight, or less than 10% by weight, when the tan remover is stored at 40° C. for three months.

The amount of urea in the tan remover may decrease by less than 20% by weight,
or less than 15% by weight, when the tan remover is stored at 40° C. for six months.

The amount of urea in the tan remover may be substantially unchanged when the tan remover is stored at 5° C. for six months. For example, the amount of urea may decrease by less than 5% by weight, or less than 4% by weight, or less than 3% by weight when the tan remover is stored at 5° C. for six months.

The amount of urea in the tan remover may be substantially unchanged when the tan remover is stored at ambient temperature, for example, 23° C., for twelve months. For example, the amount of urea may decrease by less than 5% by weight, or less than 4% by weight, or less than 3% by weight when the tan remover is stored at ambient temperature, for example, 23° C., for twelve months.

In some embodiments it has been found that while sodium bicarbonate and urea are both effective at removing artificial tan, the most preferred tan removers are those containing both components. In the absence or urea, sodium bicarbonate may leave a white powdery residue on the skin which is not cosmetically appealing. The addition of urea counteracts this and no white powdery residue is observed. Therefore, urea and sodium bicarbonate may work synergistically to improve artificial tan removal and provide a cosmetically appealing result. Further, the tan removers comprising urea and sodium bicarbonate are non-irritating to skin.

Use of the Present Artificial Tan Remover

In a sixth aspect, there is provided the use of any one of the artificial tan removers as herein disclosed for removing an artificial tan.

The use may comprise the steps of:
(a) applying topically to artificially tanned skin a tan remover as herein disclosed;
(b) leaving the tan remover in contact with the tanned skin for a time from between 1 minute and 6 hours, or between 2 minutes and 2 hours, or between 3 minutes and 1 hour; and
(c) removing the tan remover along with some or all of the artificial tan.

The time of step (b) may be less than 1 hour, or less than 30 minutes or less than 15 minutes or less than 10 minutes, or between 1 minute and 20 minutes, or between 1 minute and 15 minutes, or between 1 minute and 10 minutes, or between 1 minute and 5 minutes.

The removing may be facilitated by rinsing or wiping.

Steps (a) through (c) may be repeated if necessary.

In any of the herein disclosed uses the artificial tan remover may be applied to artificially tanned skin at any time after application of the artificial tan. For example, between 1 minute and 10 days after application of an artificial tan, or between 1 hour and 5 days, or between 1 hour and 2 days.

Methods for Removing Artificial Tan

In a seventh aspect, there is provided a method for removing an artificial tan from the skin of an individual comprising the steps of:
(a) applying topically to artificially tanned skin a tan remover as herein disclosed;
(b) leaving the tan remover in contact with the tanned skin for a time from between 1 minute and 6 hours, or between 2 minutes and 2 hours, or between 3 minutes and 1 hour; and
(c) removing the tan remover along with at least some of the artificial tan.

The time of step (b) may be less than 1 hour, or less than 30 minutes or less than 15 minutes or less than 10 minutes, or between 1 minute and 20 minutes, or between 1 minute and 15 minutes, or between 1 minute and 10 minutes, or between 1 minute and 5 minutes.

The removing may be facilitated by rinsing or wiping.

Steps (a) through (c) may be repeated if necessary.

In any of the herein disclosed methods the artificial tan remover may be applied to artificially tanned skin at any time after application of the artificial tan. For example, between 1 minute and 10 days after application of an artificial tan, or between 1 hour and 5 days, or between 1 hour and 2 days.

BRIEF DESCRIPTION OF THE FIGURE

The FIGURE illustrates Pantone® colour cards.

DESCRIPTION OF PREFERRED EMBODIMENTS

Before the present artificial tan removers, components and/or methods are disclosed and described, it is to be understood that unless otherwise indicated this invention is not limited to specific compositions, components, methods, or the like, as such may vary, unless otherwise specified. It is also to be understood that the terminology used herein is for the purpose of describing particular embodiments only and is not intended to be limiting.

It must also be noted that, as used in the specification and the appended claims, the singular forms 'a', 'an' and 'the' include plural referents unless otherwise specified. Thus, for example, reference to 'a skin penetration enhancer' may include more than one skin penetration enhancer, and the like.

Throughout this specification, use of the terms "comprises" or "comprising" or grammatical variations thereon shall be taken to specify the presence of stated features, integers, steps or components but does not preclude the presence or addition of one or more other features, integers, steps, components or groups thereof not specifically mentioned.

Disclosed herein are advantageous compositions and methods. The compositions and methods may be used for removing an artificial tan. The compositions and methods are based on an aqueous alkaline urea or substituted urea composition or aqueous base compositions. The compositions are effective at removing artificial tan quickly and in a single application.

Urea or Urea Derivative

The urea, or substituted derivative of urea, may be represented by the formula:

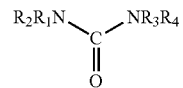

wherein $R_1$, $R_2$, $R_3$ and $R_4$ are independently selected from hydrogen, a $C_1$-$C_4$ alkyl group, a $C_1$-$C_4$ alkyl group substituted with one or more of amine, ester, carboxyl, alkoxy or halide or a $C_2$-$C_6$ hydroxyalkyl group containing from 1 to 5 hydroxyl groups.

Base

The artificial tan removers of the present disclosure may further comprise one or more bases. Preferably, the artificial tan removers may comprise one or more weak bases. The one or more bases may be used to modify the pH of the tan remover.

The one or more bases may be any pH adjuster that shifts pH above 7.0, that is, an alkaline pH adjuster. The one or more bases may be selected from metal salts, such as hydroxides, carbonates, bicarbonates or selected from phosphates, ammonia, amino acids or amines.

The one or more bases may be selected from one or more alkali metal and alkaline earth salts. The alkali metal and alkaline earth salts may be selected from one or more carbonate and bicarbonate salts. Preferred bases include alkali metal hydroxides, carbonates and bicarbonates. Exemplary bases include sodium hydroxide, sodium carbonate and sodium bicarbonate. Other exemplary bases include potassium hydroxide, sodium hydroxide, triethanolamine, 2-amino-2-hydroxymethyl-1,3-propanediol, disodium phosphate, ammonium hydroxide, trisodium citrate or tetrasodium EDTA. Amino acids may be selected from one or more amino acids, including but not limited to, arginine, lysine and histidine.

The artificial tan remover may comprise up to about 30% by weight of one or more bases, or up to about 20% by weight, or up to about 15% by weight or up to about 10% by weight, based on the total weight of the artificial tan remover. The artificial tan remover may comprise about 1 to about 10% by weight of one or more bases, or about 2 to 7% by weight of one or more bases.

Penetration Enhancers

The artificial tan remover of the present disclosure may comprise one or more skin penetration enhancers included to enhance the artificial tan removal performance. Any skin penetration enhancer known in the art for use in personal care compositions may be used herein.

The penetration enhancers may be selected from one or more, alcohols, glycols, polyols, fatty acids, surfactants, oils, ether alcohols, cyclic ether alcohols, alkoxy substituted cyclic ethers or fatty alcohol esters. Preferred alcohols include ethanol and isopropanol. Preferred glycols include propylene glycol. Preferred oils include isopropyl myristate. Preferred ether alcohols include, but are not limited to, butoxydiglycol, ethoxyethanol, methoxyethanol, phenoxydiglycol, phenoxyethanol, phenoxyisopropanol, methoxypropanol and methoxydiglycol, the most preferred being ethoxydiglycol. A preferred alkoxy substituted cyclic ether includes dimethyl isosorbide. Preferred fatty alcohol esters range between approximately $C_9$ to $C_{15}$ with the most preferred fatty alcohols ester being $C_{12}$ to $C_{15}$ alcohol benzoates, $C_{12}$ to $C_{15}$ alcohol lactates and $C_{12}$ to $C_{15}$ alcohol octanoates.

The artificial tan remover may comprise up to 30% by weight of one or more skin penetration enhancers, based on the total weight of the artificial tan remover, or up to about 20% by weight, or up to about 15% by weight. The skin penetration enhancer may be present in an amount of about 1 to about 20% by weight, or about 2 to about 15%, or about 3 to about 10%, based on the total weight of the artificial tan remover.

Surfactants

The artificial tan remover of the present disclosure may comprise a surfactant or a mixture of surfactants. Any surfactant known in the art for use in personal care compositions may be used herein.

The surfactant may be an anionic surfactant, a cationic surfactant, a non-ionic surfactant, an amphoteric surfactant, or mixtures thereof. Preferably, the surfactant is an amphoteric surfactant.

Suitable anionic surfactants include alkyl sulphates, alkyl ether sulphates, alkaryl sulphonates, alkyl succinates, alkyl sulphosuccinates, acyl taurates, acyl glutamates, N-alkoyl sarcosinates, alkyl phosphates, alkyl ether phosphates, alkyl ether carboxylates, and alpha-olefin sulphonates, especially their sodium, potassium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule, and preferably contain from 1 to 5 ethylene oxide units per molecule, more preferably contain 2 to 3 ethylene oxide units per molecule.

Examples of suitable anionic surfactants include sodium lauryl ether sulphate, sodium oleyl succinate, ammonium lauryl sulphosuccinate, ammonium lauryl sulphate, sodium dodecylbenzene sulphonate, triethanolamine and sodium salts of dodecylbenzene sulphonate and sodium N-lauryl sarcosinate.

The most preferred anionic surfactants are sodium lauryl ether sulphate 1 ethylene oxide (EO), 2EO, and 3EO, ammonium lauryl sulphate, ammonium lauryl ether sulphate 1EO, 2EO and 3EO, and triethanolamine and sodium salts of dodecylbenzene sulphonate.

Suitable cationic surfactants include quaternary ammonium salts. Cetyl-trimethylammonium chloride is a specific example of a suitable cationic surfactant. Other suitable cationic surfactants may include tetramethylammonium hydroxide or chloride, octyltrimethylammonium hydroxide or chloride, dodecyltrimethylammonium hydroxide or chloride, hexadecyltrimethyl-ammonium hydroxide or chloride, octyldimethylbenzylammonium hydroxide or chloride, decyldimethylbenxylammonium hydroxide or chloride, didodecyldimethylammonium hydroxide or chloride, dioctadecyldimethylammonium hydroxide or chloride, tallow trimethylammonium hydroxide or chloride, cocotrimethylammonium hydroxide or chloride.

Suitable non-ionic surfactants may include condensation products of aliphatic (C9-C18) primary or secondary linear or branched chain alcohols or phenols with alkylene oxides, usually ethylene oxide and generally having from 2 to 30 EO groups, more preferably at least 3 EO, still more preferably at least 5 EO, but usually not more than 25 EO, more preferably not more than 20 EO or even not more than 15 EO.

Other suitable non-ionic surfactants include alkylpolyglycosides and mono- or di-alkyl alkanolamides. Examples of the latter non-ionics include coco mono- or di-ethanolamide and coco mono-isopropanolamide.

Suitable amphoteric and zwitterionic surfactants may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl and hydroxysultaines, wherein the alkyl and acyl groups have 8 to 19 carbon atoms. Examples include lauryl amine oxide, cocodimethyl sulphopropyl betaine and preferably lauryl betaine, cocamidopropyl betaine and sodium cocamphopropionate.

The surfactant may present in the artificial tan remover in an amount of 1-50%, preferably at least 2%, more preferably at least 3%, still more preferably at least 5%, even more preferably at least 7%, but typically not more than 30%, preferably not more than 20%, by weight of the tan remover.

Preservatives

Although the present artificial tan removers have an excellent anti-microbial profile, a preservative may also be employed to further increase the shelf-life of the tan remover. A number of well-known and pharmaceutically acceptable preservatives may be used in the present tan remover, including, for example, parabens, sodium benzoate, potassium sorbate, thimerosal, chlorobutanol, benzalkonium chloride, phenoxyethanol or benzyl alcohol and combinations thereof. Benzyl alcohol and phenoxyethanol are preferred preservatives. The tan remover may also comprise one or more salts of EDTA, for example sodium salts of EDTA, such as $Na_4EDTA$. These may serve to enhance preservation.

A suitable amount of preservative will depend on a number of factors,
    including, for example, the particular preservative selected, the intended shelf-life of the tan remover, and the results of preservative effectiveness and minimum preservative studies. When used, the amount of the preservative in the tan remover will typically be from about 0.001% to about 5% by weight, preferably from about 0.01% to about 2% by weight and more preferably from about 0.01% to about 1.0% by weight of the tan remover.

Other ingredients which extend shelf life can be added such as, for
    example, antioxidants. Examples of antioxidants include butyl hydroxytoluene, ascorbyl palmitate, tocopheryl, propyl gallate, sodium metabisulfite, potassium metabisulfite and other pharmaceutically acceptable antioxidants. Typically, the antioxidant will be present in the tan remover in an amount of from about 0.01% to about 5% by weight of the tan remover.

Further Components

The tan removers of the present disclosure may contain one or more further components for ease of application and/or user feel. For example, fragrances, colourants, moisturisers, anti-inflammatory agents, essential oils, exfoliants and skin firming agents.

Non-limiting examples of essential oils include bergamot, chamomile german, chamomile maroc, chamomile roman, cinnamon zeylanicum, clove buds, eucalyptus globulus, frankincense, fennel, hyssop, juniper, lemon grass, mountain savoury, niaouli, red thyme, rosemary, rose geranium, tagestes and ylang ylang.

Illustrative but non-limiting examples of fragrances include myrcene, dihydromyrenol, citral, tagetone, cis-geranic acid, citronellic acid and mixtures thereof. Preferably, the amount of fragrance employed in the tan remover is in the range from 0.0001 to 10%, more preferably 0.002 to 5%, most preferably 0.005 to 2% by weight of the tan remover.

The tan removers of the present disclosure may also contain one or more of emollients, moisturisers, viscosity modifying agents, buffers, humectants and solubilisers. The further components are preferably miscible and compatible and do not detract from the function of urea as herein described or detract from the stability and function of the tan remover.

The solubiliser may comprise one or more of the following: Gelucire 44/14, Gelucire 50/13, Peceol, Labrafil M2125 CS, Labrafil M1944 CS, Labrasol, Tween 80, Crodasol, Brij 30, Glycerox 767, NOVOL (Oleyl Alcohol), ETOCAS (PEG-35 Castor Oil), Arlasolve (Dimethyl lsosorbide), PEG300, Maisine 35-1, Transcutol HP, Glycerin, Span 80, Span 85, Compritol 888, Propylene Glycol, Dibutyl Sebacate, Triacetin, Miglyol 810, Miglyol 812, Myvacet, Softigen 701, Softigen 767, Kolliphor HS15, Kolliphor RH40, Kolliphor RH60, Kolliphor ELP, Cetyl Palmitate, Lauroglycol 90, Lauroglycol FCC, Labrafac PG, Labrafac Lipophile WL 1349, Miranol, Soybean Oil, Corn Oil, Olive Oil, Castor Oil, Sesame Oil, Light Mineral Oil, Heavy Mineral Oil, Coconut Oil, Canola Oil, Dimethyl Sulfoxide (DMSO), N-Methylpyrrolidone (NMP), Benzyl Benzoate, Capryol 90, Capryol PGMC, Glyceryl Monostearate, Vitamin E TPGS and Benzyl Alcohol. This list is exemplary, and other appropriate solubilisers, known to those skilled in the art to enhance aqueous solubility may be used.

The tan remover may contain one or more moisturisers or anti-irritants, such as, for example, glycerine, *Aloe barbadensis* leaf juice extract of sodium pyrrolidone carboxylate. The amount of moisturizer or anti-irritant may be between 0.01 and 5% by weight.

The tan removers may contain one or more solvents in addition to water. The solvents are preferably soluble in water. Exemplary solvents include alcohols and polyols. Non-limiting examples of solvents include ethylene glycol and propylene glycol.

The tan remover may also contain one or metal ions which may assist in the tan removal capabilities. The metal ions may be ions of copper, iron, zinc, calcium and magnesium. The metal ions are preferably in the form of water soluble salts. The metal ions may be in the form of one or more metal complexes.

Up to about 10% by weight of metal ions may be present in the tan remover, preferably up to about 5% by weight, based on the total weight of the tan remover.

Vehicle

The vehicle of the presently disclosed tan remover is preferably suitable for use in applications that require direct contact with human skin.

The tan remover is preferably in a form of a cream, foam, gel, lotion, solution, emulsion, pomade, mousse, balm, pump spray, aerosol spray, soap bar, a wipe or any combinations thereof.

Preferred embodiments of the present disclosure include:
An artificial tan remover comprising:
about 4-20% by weight of urea;
about 2-15% by weight of a bicarbonate or carbonate salt; and
the balance as water;
wherein the tan remover has a pH greater than 7.0.
An artificial tan remover comprising:
about 4-20% by weight of urea;
about 2-15% by weight of a bicarbonate or carbonate salt; and
the balance as water;
wherein the tan remover has a pH greater than 8.0.
An artificial tan remover comprising:
about 4-20% by weight of urea;
about 2-15% by weight of a bicarbonate or carbonate salt; and
the balance as water;
wherein the tan remover has a pH greater than 9.0.
An artificial tan remover comprising:
about 4-20% by weight of urea;
about 2-15% by weight of a bicarbonate or carbonate salt; and
the balance as water;
wherein the tan remover has a pH greater than 8.0; and
wherein the amount of urea in the tan remover decreases by less than 20% by weight, or less than 15% by weight, or less than 10% by weight, or less than 5% by weight, when the tan remover is stored at 40° C. for one month.

The amount of urea in the tan remover may decrease by less than 20% by weight, or less than 15% by weight, or less than 10% by weight, or less than 8% by weight, when the tan remover is stored at 40° C. for two months.

The amount of urea in the tan remover may decrease by less than 20% by weight, or less than 15% by weight, or less than 10% by weight, when the tan remover is stored at 40° C. for three months.

The amount of urea in the tan remover may decrease by less than 20% by weight, or less than 15% by weight, when the tan remover is stored at 40° C. for six months.

The amount of urea in the tan remover may be substantially unchanged when the tan remover is stored at 5° C. for six months. For example, the amount of urea may decrease by less than 5% by weight, or less than 4% by weight, or less than 3% by weight when the tan remover is stored at 5° C. for six months.

The amount of urea in the tan remover may be substantially unchanged when the tan remover is stored at ambient temperature, for example, 23° C., for twelve months. For example, the amount of urea may decrease by less than 5% by weight, or less than 4% by weight, or less than 3% by weight when the tan remover is stored at ambient temperature, for example, 23° C., for twelve months.

Further preferred embodiments of the present disclosure include:
An artificial tan remover comprising:
about 8-12% by weight of urea;
about 3-7% by weight of a bicarbonate or carbonate salt; and
the balance as water;
wherein the tan remover has a pH greater than 7.0.

An artificial tan remover comprising:
about 8-12% by weight of urea;
about 3-7% by weight of a bicarbonate or carbonate salt; and
the balance as water;
wherein the tan remover has a pH greater than 8.0.

An artificial tan remover comprising:
about 8-12% by weight of urea;
about 3-7% by weight of a bicarbonate or carbonate salt; and
the balance as water;
wherein the tan remover has a pH greater than 9.0.

An artificial tan remover comprising:
about 8-12% by weight of urea;
about 3-7% by weight of a bicarbonate or carbonate salt; and
the balance as water;
wherein the tan remover has a pH greater than 8.0; and
wherein the amount of urea in the tan remover decreases by less than 20% by weight, or less than 15% by weight, or less than 10% by weight, or less than 5% by weight, when the tan remover is stored at 40° C. for one month.

The amount of urea in the tan remover may decrease by less than 20% by weight, or less than 15% by weight, or less than 10% by weight, or less than 8% by weight, when the tan remover is stored at 40° C. for two months.

The amount of urea in the tan remover may decrease by less than 20% by weight, or less than 15% by weight, or less than 10% by weight, when the tan remover is stored at 40° C. for three months.

The amount of urea in the tan remover may decrease by less than 20% by weight, or less than 15% by weight, when the tan remover is stored at 40° C. for six months.

The amount of urea in the tan remover may be substantially unchanged when the tan remover is stored at 5° C. for six months. For example, the amount of urea may decrease by less than 5% by weight, or less than 4% by weight, or less than 3% by weight when the tan remover is stored at 5° C. for six months.

The amount of urea in the tan remover may be substantially unchanged when the tan remover is stored at ambient temperature, for example, 23° C., for twelve months. For example, the amount of urea may decrease by less than 5% by weight, or less than 4% by weight, or less than 3% by weight when the tan remover is stored at ambient temperature, for example, 23° C., for twelve months.

Further preferred embodiments of the present disclosure include:

An artificial tan remover comprising:
about 2-7% by weight of urea;
about 1-5% by weight of a bicarbonate or carbonate salt; and
the balance as water;
wherein the tan remover has a pH greater than 7.0.

An artificial tan remover comprising:
about 2-7% by weight of urea;
about 1-5% by weight of a bicarbonate or carbonate salt; and
the balance as water;
wherein the tan remover has a pH greater than 8.0.

An artificial tan remover comprising:
about 2-7% by weight of urea;
about 1-5% by weight of a bicarbonate or carbonate salt; and
the balance as water;
wherein the tan remover has a pH greater than 9.0.

An artificial tan remover comprising:
about 2-7% by weight of urea;
about 1-5% by weight of a bicarbonate or carbonate salt; and
the balance as water;
wherein the tan remover has a pH greater than 8.0; and
wherein the amount of urea in the tan remover decreases by less than 20% by weight, or less than 15% by weight, or less than 10% by weight, or less than 5% by weight, when the tan remover is stored at 40° C. for one month.

The amount of urea in the tan remover may decrease by less than 20% by weight, or less than 15% by weight, or less than 10% by weight, or less than 8% by weight, when the tan remover is stored at 40° C. for two months.

The amount of urea in the tan remover may decrease by less than 20% by weight, or less than 15% by weight, or less than 10% by weight, when the tan remover is stored at 40° C. for three months.

The amount of urea in the tan remover may decrease by less than 20% by weight, or less than 15% by weight, when the tan remover is stored at 40° C. for six months.

The amount of urea in the tan remover may be substantially unchanged when the tan remover is stored at 5° C. for six months. For example, the amount of urea may decrease by less than 5% by weight, or less than 4% by weight, or less than 3% by weight when the tan remover is stored at 5° C. for six months.

The amount of urea in the tan remover may be substantially unchanged when the tan remover is stored at ambient temperature, for example, 23° C., for twelve months. For example, the amount of urea may decrease by less than 5% by weight, or less than 4% by weight, or less than 3% by weight when the tan remover is stored at ambient temperature, for example, 23° C., for twelve months.

Further preferred embodiments of the present disclosure include:

An artificial tan remover comprising:
about 3-7% by weight of a bicarbonate or carbonate salt; and
the balance as water;
wherein the tan remover has a pH greater than 7.0.

An artificial tan remover comprising:
about 3-7% by weight of a bicarbonate or carbonate salt; and
the balance as water;
wherein the tan remover has a pH greater than 8.0.

An artificial tan remover comprising:
about 3-7% by weight of a bicarbonate or carbonate salt; and
the balance as water;
wherein the tan remover has a pH greater than 9.0.

The tan removers of any one of the preferred embodiments may contain one or more of the further components as disclosed herein.

Further preferred embodiments of the tan remover of the present disclosure comprise the components as outlined in Tables 1, 2, and 3.

TABLE 1

| Component | Range (% by weight) |
|---|---|
| Water | 40-80 |
| Urea | 0.1-20 |
| Penetration enhancer | 0-40 |
| Base | 0.1-10 |
| Surfactant | 3-20 |
| Other components | 0-20 |

TABLE 2

| Component | Range (% by weight) |
| --- | --- |
| Water | 50-70 |
| Urea | 5-20 |
| Penetration enhancer | 3-30 |
| Base | 1-10 |
| Surfactant | 3-20 |
| Other components | 0-20 |

TABLE 3

| Component | Composition 63/14/3 % by weight |
| --- | --- |
| 10 | 64.7 |
| Urea | 10.0 |
| Cocoamidopropyl betaine | 10.0 |
| Sodium bicarbonate | 5.0 |
| Ethoxydiglycol | 6.0 |
| PEG-40 hydrogenated castor oil | 1.8 |
| Glycerine | 1.5 |
| Tetrasodium EDTA | 0.6 |
| Fragrance | 0.3 |
| *Aloe Barbadensis* leaf juice | 0.10 |
| Sodium Hydroxide | QS[1] to pH 9.0-9.6 |
| Total | 100.0 |

QS[1] = quantum satis (sodium hydroxide added in amount sufficient to achieve desired pH)

The tan removers of Tables 1, 2 and 3 may contain one or more of the further components as disclosed herein.

EXAMPLES

The following Examples describe the artificial tan removers according to the present disclosure and are intended to illustrate the disclosure. The Examples are not to be construed as limiting in any way the scope of the present disclosure.

The method by which the artificial tan removers of the present disclosure are prepared is not critical. A preferred method comprises mixing the components at ambient temperature with stirring to provide a single-phase solution.

A retail artificial tanning product based on dihydroxyacetone was applied to skin in a defined area of the forearm. The product was left on the skin for 1-3 days, including exposure to daily showers. A tan remover according to the present disclosure was then applied to the tanned area and left for 1-10 mins. After this time, the skin was rinsed with warm water.

Using the defined area of the forearm which had the artificial tan applied 1-3 days prior as a colour control, the efficacy of colour removal of the tan removers of the present disclosure was visually assessed and ranked on a scale of 1 (poor removal of colour compared to the control area) to 5 (excellent removal of colour compared to the control area) and further compared with the colour of a Pantone® colour card as shown in the FIGURE.

Comparison Between Acidic and Basic Tan Removers

The acidic and basic (alkaline) tan removers as detailed in Table 4 were subjected to the above described artificial tan removal test. Two comparative compositions containing an alphahydroxy acid blend and having a pH of about 4 were compared to a tan remover according to the present disclosure comprising urea and sodium bicarbonate of pH about 9.

TABLE 4

| | Composition # | | |
| --- | --- | --- | --- |
| | F32/17/20 % by weight | F32/16/3 % by weight | F32/17/21 % by weight |
| Water | 78.8 | 64.0 | 75.7 |
| Multifruit BSC ® (alphahydroxy acid blend) | 10.0 | 10.0 | 0 |
| Sodium bicarbonate | 0 | 0 | 6.0 |
| Urea | 5 | 0 | 10.8 |
| Propylene glycol and *Aloe Barbadensis* extract | 2.0 | 0 | 2.2 |
| Glycerine | 1.5 | 0 | 0 |
| Ethoxydiglycol | 0 | 25.0 | 0 |
| Laureth-4 | 0 | 0 | 4.0 |
| Benzyl alcohol | 1.0 | 0 | 1.1 |
| Xanthan Gum | 0 | 1.0 | 0 |
| Magnesium Aluminum Silicate | 1.5 | 0 | 0 |
| Allantoin | 0.2 | 0 | 0.2 |
| Total | 100.0 | 100.0 | 100.0 |
| pH | 4.08 | 4.44 | 8.89 |
| Visual colour ranking | 3 | 3 | 5 |
| Pantone Colour | PMS722 | PMS4645 | PMS4665 |

The colour assessment in Table 4 indicates that the basic (alkaline) tan remover is more effective than the acid compositions in removing the colour of the artificial tan. The control Pantone® colour is PMS4635.

Comparison Between Alkali Metal Salt and Urea Tan Removers

Tan removers according to the present disclosure containing urea, sodium bicarbonate, and a mixture of both, were compared to a tan remover (63/16/2) absent urea and sodium bicarbonate and in which alkalinity was effected by the addition of sodium hydroxide. The tan removers and results are summarized in Table 5. The control colour, after two days without a tan remover applied, is Pantone® colour PMS4635.

TABLE 5

| | Composition # | | | |
| --- | --- | --- | --- | --- |
| | 63/18/3 % by weight | 63/20/9 % by weight | 63/14/3 % by weight | 63/16/2 % by weight |
| Water | 74.8 | 71.9 | 64.7 | 87.9 |
| Sodium bicarbonate | 5.0 | 0 | 5.0 | 0 |
| Urea | 0 | 10.0 | 10.0 | 0 |
| Glycerine | 1.5 | 1.5 | 1.5 | 1.0 |
| Ethoxydiglycol | 6.0 | 6.0 | 6.0 | 7.5 |
| Cocoamidopropyl betaine (30% solution) | 10.0 | 10.0 | 10.0 | 0 |
| Tetrasodium EDTA | 0.6 | 0.6 | 0.59 | 0 |
| *Aloe Barbadensis* leaf juice | 0 | 0 | 0.16 | 0 |
| Fragrance | 0.3 | 0 | 0.3 | 0.4 |
| PEG-40 hydrogenated castor oil | 1.8 | 0 | 1.8 | 2.3 |
| Sodium hydroxide | QS[1] to 9.0-9.6 | | | Added to give pH in 9.0 to 9.6 range |
| Total | 100.0 | 100.0 | 100.0 | 100.0 |
| pH | 9.0 | 9.6 | 9.6 | 9.2 |
| Visual colour ranking | 5 | 4 | 5 | 2 |
| Pantone Colour | PMS4655 | PMS4665 | PMS4665 | PMS4645 |

QS[1] = quantum satis (sodium hydroxide added in amount sufficient to achieve desired pH)

Each of sodium bicarbonate and urea alone are effective agents for colour removal and both are more effective than sodium hydroxide. However, while sodium bicarbonate alone is effective, it may leave a white powdery residue on the skin which is cosmetically undesirable. The addition of urea counteracts this and no white powdery residue is observed.

The effect of base type was studied by adding various bases to the composition of Table 6:

TABLE 6

| Component | Composition (% by weight) |
|---|---|
| Water | 82.5 |
| Glycerine | 1.5 |
| Ethoxydiglycol | 6.0 |
| Cocamidopropyl Betaine | 10.0 |
| Total | 100.0 |

Table 7 summarises the details and results:

TABLE 7

| Composition # | Base | pH | Relative Tan Removal | Ranking | Pantone Colour |
|---|---|---|---|---|---|
| F/L63-22-8 | Sodium Bicarbonate | 8.19 | Very good | 4 | PMS4665 |
| F/L63-22-10 | Triethanolamine | 9.05 | Good | 3 | PMS4665 |
| F/L63-22-17 | Sodium carbonate | 9.23 | Fair | 3 | PMS4655 |
| F/L63-22-7 | Sodium carbonate | 11.36 | Very good | 4 | PMS4665 |
| F/L63-22-14 | Sodium Phosphate Dibasic | 8.49 | Fair | 2 | PMS4655 |
| F/L63-22-19 | EDTA | 9.26 | Fair | 2 | PMS4655 |
| F/L63-22-13 | EDTA | 9.74 | Fair | 2 | PMS4655 |
| F/L63-22-23 | Sodium hydroxide | 9.25 | Fair | 2 | PMS4655 |
| F/L63-22-6 | No base (comparative) | 4.74 | Poor | 1 | PMS4645 |

All the bases tested demonstrated ability to remove the artificial tan, relative to the comparative example having no added base. The best performing bases were sodium bicarbonate and sodium carbonate. Sodium bicarbonate is most preferred as it provides a composition of significantly lower pH than sodium carbonate.

Table 8 details examples of compositions prepared according to the present disclosure.

TABLE 8

| Component | Composition 63/1/1 (% by weight) | Composition 63/1/2 (% by weight) |
|---|---|---|
| Water | 64.4 | 64.4 |
| Sodium carbonate | 5.0 | 0 |
| Sodium bicarbonate | 0 | 5.0 |
| Urea | 10.0 | 10.0 |
| Propylene glycol and *Aloe Barbadensis* | 2.0 | 2.0 |
| Glycerine | 1.5 | 1.5 |
| Ethoxydiglycol | 6.0 | 6.0 |
| Benzyl alcohol | 1.0 | 1.0 |
| Cocamidopropyl Betaine | 10.0 | 10.0 |
| Tetrasodium EDTA | 0.1 | 0.1 |
| Total | 100.0 | 100.0 |
| pH | 11.12 | 8.78 |

The compositions of Table 8 were both found to be highly effective in removing artificial tanning products.

Table 9 summarises the results of a long-term shelf-life study of the compositions of Table 8.

TABLE 9

| Base | 0 | 1 | 2 | 3 | 6 |
|---|---|---|---|---|---|
| | Urea wt. % vs. Months Storage at 40° C. | | | | |
| Sodium carbonate | 9.86 | 9.54 | 9.26 | 9.16 | 8.59 |
| Sodium bicarbonate | 10.00 | 9.74 | 9.43 | 9.32 | 8.86 |
| | % Change in Urea wt. % vs. Months Storage at 40° C. | | | | |
| Sodium carbonate | — | −3.2 | −6.1 | −7.1 | −12.9 |
| Sodium bicarbonate | — | −2.6 | −5.7 | −6.8 | −11.4 |

It is evident that the compositions possess excellent stability in an accelerated storage test conducted in accordance with standard practice. The amount of urea decreased by less than or equal to 10% by weight when the compositions were stored for 3 months at 40° C. This is unexpected and highly advantageous in terms of maintaining efficacy of tan removal performance over time.

When stored at 5° C. for six months the artificial tan removers of the present disclosure showed no appreciable change in the amount of urea.

When stored at 25° C. or 40° C. for six months the artificial tan removers retained their excellent ability to remove artificial tan, as detailed in Table 10.

TABLE 10

| Composition # | Description | pH | Relative tan removal | Ranking | Pantone colour |
|---|---|---|---|---|---|
| F/L63-1-2 | 25° C. sample at 6 months | 8.88 | Very good | 4 | PMS4665 |
| F/L63-1-2 | 40° C. sample at 6 months | 9.1 | Very good | 4 | PMS4665 |

In a further example, an artificial tan remover comprising components as formulation 63/14/3 in Table 5 was stored for 12 months at 23° C. The initial pH of the composition was 9.00. After 12 months the pH was 9.08. The amount of urea in the composition after storage for 12 months was not measurably different to that present in the starting composition. The result indicates that aqueous urea compositions having high long term stability to urea decomposition and minimal, if any, pH drift may be produced.

It is to be understood that while the present disclosure has been described in conjunction with the specific embodiments thereof, the foregoing description is intended to illustrate and not limit the scope of the disclosure. Other aspects, advantages and modifications will be apparent to those skilled in the art to which the disclosure pertains. Therefore, the above examples are put forth to provide those skilled in the art with a complete disclosure and description of how to make and use the disclosed compositions, and are not intended to limit the scope of the disclosure.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited.

All documents cited are herein fully incorporated by reference for all jurisdictions in which such incorporation is permitted and to the extent such disclosure is consistent with the description of the present disclosure.

The invention claimed is:

1. An artificial tan remover composition comprising consisting of:
    10% by weight of urea;
    5% by weight of sodium bicarbonate;
    6% by weight of ethoxydiglycol;
    64.7% by weight of water;
    1.5% by weight of glycerine;
    10% by weight of a 30% cocamidopropyl betaine solution;
    0.59% by weight of tetrasodium EDTA;
    0.16% by weight of *Aloe barbadensis* leaf juice;
    0.3% by weight of a fragrance;
    1.8% by weight of PEG-40 hydrogenated castor oil and;
    sodium hydroxide in an amount sufficient to provide said artificial tan remover composition with a pH of 9.0-9.6;
    and wherein said composition removes artificial tan and does not require abrasion or exfoliation.

2. The artificial tan remover composition according to claim 1,
    wherein the amount of urea in the tan remover decreases by less than 20% by weight when the tan remover is stored at 40° C. for one month.

3. The artificial tan remover composition according to claim 1,
    wherein the amount of urea in the tan remover decreases by less than 20% by weight, when the tan remover is stored at 40° C. for two months.

4. The artificial tan remover composition according to claim 1,
    wherein the amount of urea in the tan remover decreases by less than 20% by weight, when the tan remover is stored at 40° C. for three months.

5. The artificial tan remover composition according to claim 1,
    wherein the amount of urea in the tan remover decreases by less than 20% by weight when the tan remover is stored at 40° C. for six months.

6. The artificial tan remover composition according to claim 1,
    wherein the amount of urea in the tan remover decreases by less than 20% by weight, when the tan remover is stored at 23° C. for twelve months.

7. The artificial tan remover composition according to claim 1,
    wherein the tan remover is in the form of a liquid, a lotion, a gel, a cream, a foam, a solution, an emulsion, a pomade, a mousse, a balm, a pump spray, a wipe, a soap bar or an aerosol spray.

8. The artificial tan remover composition according to claim 1,
    wherein the amount of urea in the tan remover decreases by less than 15% by weight when the tan remover is stored at 40° C. for one month.

9. The artificial tan remover composition according to claim 1,
    wherein the amount of urea in the tan remover decreases by less than 10% by weight when the tan remover is stored at 40° C. for one month.

10. The artificial tan remover composition according to claim 1,
    wherein the amount of urea in the tan remover decreases by less than 5% by weight when the tan remover is stored at 40° C. for one month.

11. The artificial tan remover composition according to claim 1,
    wherein the amount of urea in the tan remover decreases by less than 15% by weight when the tan remover is stored at 40° C. for two months.

12. The artificial tan remover composition according to claim 1,
    wherein the amount of urea in the tan remover decreases by less than 10% by weight when the tan remover is stored at 40° C. for two months.

13. The artificial tan remover composition according to claim 1,
    wherein the amount of urea in the tan remover decreases by less than 5% by weight when the tan remover is stored at 40° C. for two months.

14. The artificial tan remover composition according to claim 1,
    wherein the amount of urea in the tan remover decreases by less than 15% by weight when the tan remover is stored at 40° C. for three months.

15. The artificial tan remover composition according to claim 1,
    wherein the amount of urea in the tan remover decreases by less than 10% by weight when the tan remover is stored at 40° C. for three months.

16. The artificial tan remover composition according to claim 1,
    wherein the amount of urea in the tan remover decreases by less than 15% by weight when the tan remover is stored at 40° C. for six months.

17. The artificial tan remover composition according to claim 1,
    wherein the amount of urea in the tan remover decreases by less than 15% by weight when the tan remover is stored at 23° C. for twelve months.

18. The artificial tan remover composition according to claim 1,
    wherein the amount of urea in the tan remover decreases by less than 10% by weight when the tan remover is stored at 23° C. for twelve months.

19. The artificial tan remover composition according to claim 1,
    wherein the amount of urea in the tan remover decreases by less than 5% by weight when the tan remover is stored at 23° C. for twelve months.

20. The artificial tan remover composition according to claim 1,
    wherein the amount of urea in the tan remover decreases by less than 2% by weight when the tan remover is stored at 23° C. for twelve months.

* * * * *